(12) United States Patent
Kurokawa et al.

(10) Patent No.: US 7,440,112 B2
(45) Date of Patent: Oct. 21, 2008

(54) METHOD AND AN APPARATUS FOR SHAPE MEASUREMENT, AND A FREQUENCY COMB LIGHT GENERATOR

(75) Inventors: Takashi Kurokawa, Fuchu (JP); Yousuke Tanaka, Fuchu (JP); Tatsutoshi Shiota, Fuchu (JP)

(73) Assignees: National University Corporation, Tokyo (JP); Tokyo University of Agriculture and Technology, Tokyo (JP)

( * ) Notice: Subject to any disclaimer, the term of this patent is extended or adjusted under 35 U.S.C. 154(b) by 0 days.

(21) Appl. No.: 11/659,951

(22) PCT Filed: Aug. 17, 2005

(86) PCT No.: PCT/JP2005/015309

§ 371 (c)(1),
(2), (4) Date: Feb. 12, 2007

(87) PCT Pub. No.: WO2006/019181

PCT Pub. Date: Feb. 23, 2006

(65) Prior Publication Data

US 2008/0018906 A1    Jan. 24, 2008

(30) Foreign Application Priority Data

Aug. 18, 2004  (JP)  ............................... 2004-238902

(51) Int. Cl.
*G01B 9/02* (2006.01)
(52) U.S. Cl. .................................................... 356/495

(58) Field of Classification Search ................. 356/477, 356/491, 492, 495; 250/227.19, 227.27; 385/12
See application file for complete search history.

(56) References Cited

U.S. PATENT DOCUMENTS 6,493,091 B2 *  12/2002  Kourogi et al. ............. 356/489
6,897,959 B2 *   5/2005  Haensch et al. ............. 356/432

FOREIGN PATENT DOCUMENTS

| JP | 2002-082045 | 3/2002 |
| JP | 2003-043434 | 2/2003 |
| JP | 2003-043435 | 2/2003 |

\* cited by examiner

*Primary Examiner*—Michael A Lyons
(74) *Attorney, Agent, or Firm*—Manabu Kanesaka

(57) ABSTRACT

A method and an apparatus for shape measurement that is able to observe the deep portion under a skin with high spatial resolution by using a frequency COMB light generator is provided. A frequency COMB light generator for generating multiple frequency COMBs with variable frequency pitch at high operation stability is provided.

This apparatus for shape measurement comprises a frequency COMB light generator and an optical interferometer for measuring the distance. The frequency COMB light generator includes a laser light source 11, an optical resonator 13, a COMB pitch regulator 14 and an output port OUT. The optical resonator 13 includes an optical modulator 131, a first mirror M11, an optical fiber F13 which is drawn out from alight waveguide of the optical modulator. The COMB pitch regulator 14 is a modulation signal generator for varying the modulation signal. The optical fiber F13 is equipped with an apparatus (Faraday rotation mirror) for compensating a change in the polarization condition.

12 Claims, 13 Drawing Sheets

OFC
(spectrum of frequency COMB light)

METHOD AND AN APPARATUS FOR SHAPE MEASUREMENT, AND A FREQUENCY COMB LIGHT GENERATOR

TECHNICAL FIELD

This invention relates to a method and an apparatus for shape measurement that is able to observe the deep portion under a skin with high spatial resolution by using a frequency COMB light generator. This invention also relates to a frequency COMB light generator for generating multiple frequency COMBs with variable frequency pitch at high operation stability.

BACKGROUND ART

The Optical Coherence Tomography (OCT) is known for obtaining a tomogram of the structure under a skin by applying the light through a living body skin and detecting the reflected light from an internal anatomy) See Japanese Patent Application Laid-Open No. 2004-191114).

FIG. 11(A) shows a prior art an optical coherence tomography system. In FIG. 11(A), an optical coherence tomography system 8 includes a low coherence light source 81, a condensing lens 82, a half-mirror 83, a reference mirror 84, an actuator for moving the reference mirror 85, an object lens 86, a detecting lens 87, a light detector 88 and a control computer 89.

The elements of the optical coherence tomography system 8 excepting the low coherence light source 81 and the computer 89 constitutes an optical interferometer. A light source with a wide spectrum width like LED, SLD (Super Luminescent Diode), etc. is used as the low coherence light source 81 and has a spread wave length spectrum (e.g. tens nm or wider) as shown in FIG. 11(B).

The low coherence light source 81 is controlled by a control signal A1 from the computer 89. The light from the low coherence light source 81 is collimated by the condensing lens 82 and is output to the half mirror 83. The half-mirror 83 splits the light from the condensing lens 82 into two parts, directs one part to the reference mirror 84 and directs the other part to a measured object O through the object lens 86.

The half-mirror 83 also combines the reflected light from the reference mirror 84 with the reflected light from a reflection point within the measured object O and outputs the combined light to the light detector 88 through the detecting lens 87.

The reflected light from the measured object O includes the light reflected at the surface, the light reflected at a shallow internal point and the light reflected at a deep internal point.

Since the light uses for detection is a low coherence light, the reflected light which experienced an interference includes only the reflected light from the plane at the position where the distance form the half-mirror 83 is $(L_0 \pm L_0'/2)$, where $L_0$ is the distance between the half-mirror 83 and the reference 84 and $L_0'$ is the coherence length.

By changing the distance between the half-mirror 83 and the reference 84 by the actuator 85 (controlled by a control signal A2 from the computer 89) it is possible to selectively detect only the reflected light from the reflection plane that corresponds to the distance.

By this technique it is possible to calculate the reflection index at any position inside the measured object O by the computer 89 and provide the visual internal structure information for the measured object O by displaying the distribution of the calculated reflection index onto a display screen (not shown).

DISCLOSURE OF INVENTION

The output of the low coherence light source 81 in FIG. 11(A) has a wide spectrum width as mentioned above (See FIG. 11(B)). Although the spatial resolution in the depth direction is high in the optical coherence tomography 8, the deep portion inside the measured object O cannot be observed because the light intensity is low and the output level is very low due to the low efficiency. Furthermore the observation by this system is time consuming and the creditability is not necessarily high because the reference mirror is movable.

It has been studying to improve the spatial resolution by using a femto-second laser with a wide spectrum width as a light source of an optical coherence tomography system. However, this type of optical coherence tomography system becomes big and expensive, and therefore it is not suitable for usage in clinics.

A technique for synthesizing a hypothetical frequency COMB light as a time average like a coherence function synthesizing method is known. However the application of this technique is limited to distance measurement like a fiber-sensing because the frequency pitch cannot be shortened and the number of generated COMBs is limited (See Japanese Patent Application Laid-Open No. 10-148596) and therefore this technique is not suitable for shape measurement like observation of the anatomy under a living body skin.

A prior art frequency COMB light generator 9 shown in FIG. 12(A) includes a laser light source 91 and an optical resonator 92. The optical resonator 92 includes an optical modulator 922 formed on a LN(LiNbO$_3$) substrate 921 and mirrors M01, M02. The output signal (angular frequency $\omega_0$) of a laser light source 91 is modulated and frequency shifted by a modulation signal RF0 in the optical resonator 92, and then repeatedly reflected by the mirrors M01, M02 and repeatedly modulated, The optical resonator 92 outputs the laser light (modulated light ML) shown in the drawing.

This modulated light ML is shown in FIG. 12(A) as a frequency component FE and includes discretely multiple frequency components as shown in FIG. 12(B). As shown in these drawings, the center of angular frequencies is at $\omega_0$ and the distribution of the angular frequencies has a higher frequency side band and a lower frequency side band.

However it was difficult to make the frequency pitch of the frequency COMBs variable because the frequency pitch of the frequency COMBs is determined by the distance between mirrors M01 and M02 in the frequency COMB light generator 9.

A purpose of the present invention is to provide a method and an apparatus like an optical coherence tomography system for observing the anatomy under a living body skin with a high depth spatial resolution to a deep position by using a frequency COMB light generator which is capable of changing the frequency pitch of the frequency COMBs as an optical source.

Another purpose of the present invention is to provide a frequency COMB light generator which is capable of operation with high stability, variable frequency pitch of frequency COMBs and generation of multiple frequency COMBs by using a simple configuration.

BEST MODE FOR CARRYING OUT THE INVENTION

Figure 1:
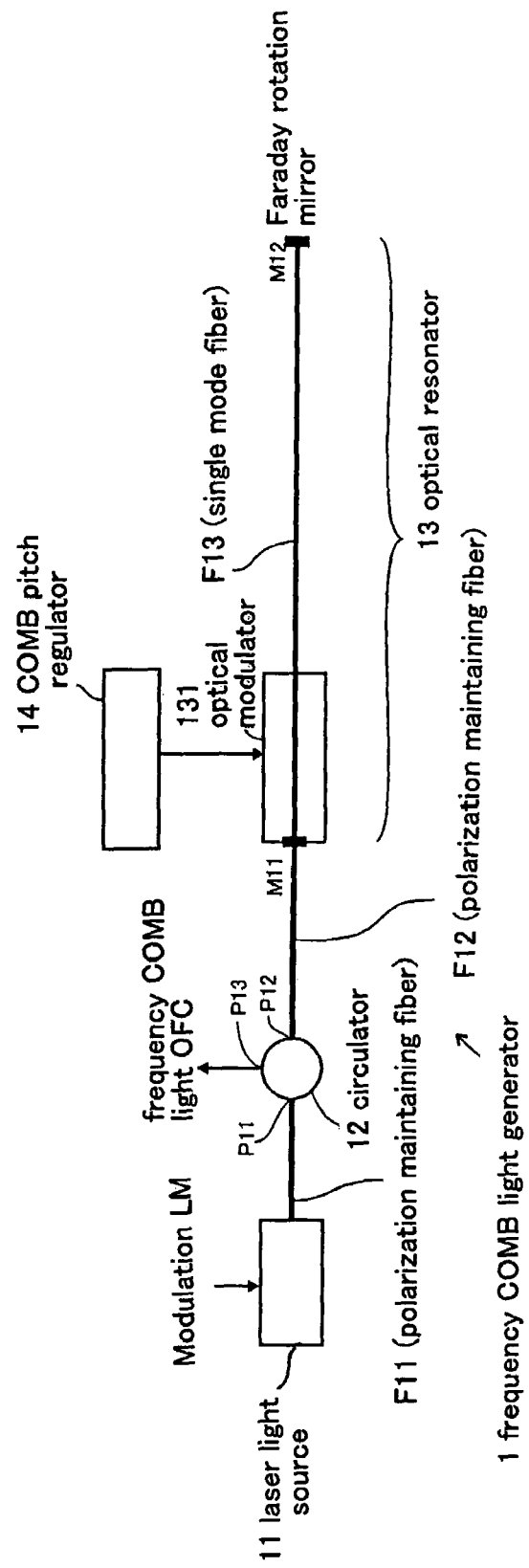
FIG. 1 is shows a first embodiment of a frequency COMB light generator according to the present invention.

FIG. 1 is shows a first embodiment of a frequency COMB light generator according to the present invention. In FIG. 1, the frequency COMB light generator 1 includes a laser light source 11, a circulator 12, an optical resonator 13 and a COMB pitch regulator 14.

In this embodiment, the laser light source 11 can output a laser light (center angular frequency $\omega_0$) in a wavelength band (e.g. 1.2~1.6 μm) where the penetration efficiency inside a living body is high.

In FIG. 1, a modulation signal LM is input into the laser light source 11 and the output of the laser light source 11 can have a predetermined width (e.g. a width from hundreds MHz to GHz) for the center frequency $\omega_0$.

The circulator 12 is located between the laser light source 11 and the optical resonator 13, and the laser light source 11 is connected to a first port P11 through an optical fiber F11 (polarization maintaining fiber) and the optical resonator 13 is connected to a second port P12 through an optical fiber F12 (polarization maintaining fiber). The input light to the first port P11 is output from the second port P12, and the input light to the second port P12 is output from a third port P13. The third port P13 is an output port from the frequency COMB light OFC that will be explained later.

The optical resonator 13 generates the frequency COMB light OFC based on the laser light (center frequency $\omega_0$) that is output from the laser light source 11. The optical resonator 13 includes an optical modulator 131, a first mirror M11 and a second mirror M12.

The COMB pitch regulator 14 is a modulation signal generator for varying a modulation signal fed to the modulation electrode of the optical resonator 13, and the angular frequency pitch $\Omega$ can be varied or swept by varying the modulation frequency.

The first mirror M11 is located at one side of the optical modulator 131 where the circulator 12 is situated, and the second mirror M12 is connected to the other side of the optical modulator 131 through a predetermined length (the distance L between the mirror M12 and the mirror M11) of the optical fiber F13 (single mode (SM) fiber).

In this embodiment, the second mirror M12 is a Faraday rotation mirror. The single mode fiber causes a change in the polarization condition of the transmitted light. The polarization plane is 45° rotated at the input and the output respectively, i.e. 90° rotated relative to the original light eventually) by the Faraday rotation mirror (second mirror M12) that is located at the end of the optical fiber F13. As a result, the change in polarization condition that caused in the optical fiber F13 is accurately compensated.

The length of the optical fiber F13 is set such that the distance L between the first mirror M11 and the second mirror M12 becomes integral multiple (m) of a half of the wave length ($\lambda/2$). L is give by the following equation, where "n" is the refractive index of the optical fiber F13 and "c" is the light speed.

$$L = m \times (\lambda/2) \times (1/n) = (m/n) \times (c\pi/\omega_0)$$

Figure 2A:
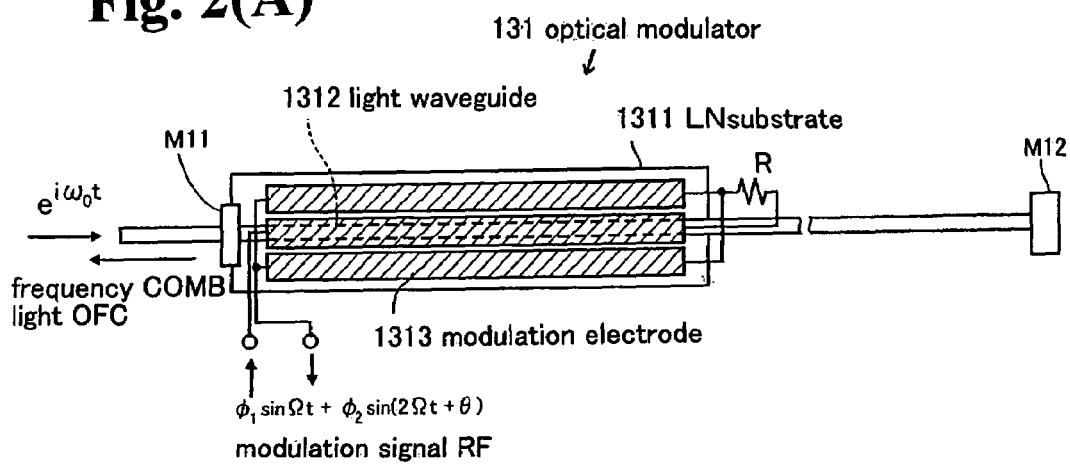
FIG. 2(A) shows a first example of an optical modulator in the frequency COMB light generator shown in FIG. 1; (B) shows a perspective view of the optical modulator shown in (A); (C) shows a spectrum of the output light from the optical modulator shown in (A) and (B).
Figure 2B:
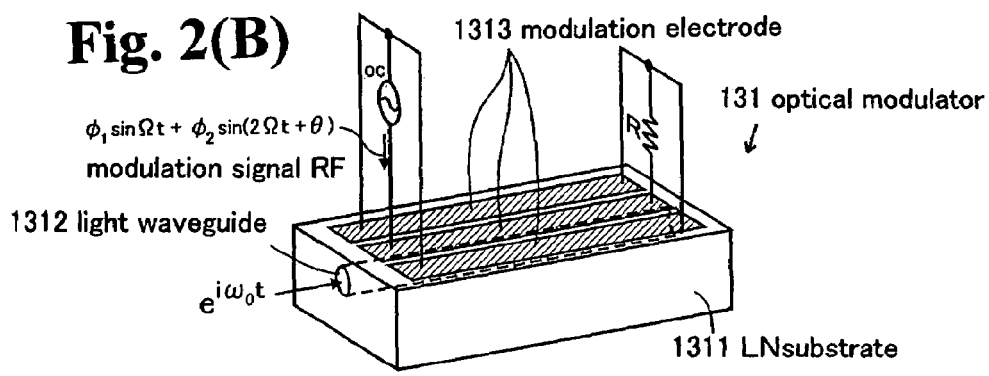

The first example of the optical modulator 131 will be explained referring to the plane view of FIG. 2(A) and the perspective view of FIG. 2(B). In FIGS. 2(A) and (B), the optical modulator 131 includes a LN (LiNbO$_3$) substrate 1311, a light waveguide 1312 formed on the substrate 1311 and the modulation electrode 1313. FIG. 2(A) shows the mirror M11 and the mirror M12, and FIG. 2(B) shows a modulation drive circuit constituted of an oscillator 0C and a terminal resistor R. In FIGS. 2(A) and (B), a laser light (represented by "exp(i $\omega_0$t)") is input into the optical modulator 131 and the modulation signal RF is fed from the oscillator 0C to the modulation electrode 1313. The modulation signal RF is represented by the following expression.

$$\phi_1 \sin \Omega t + \phi_2 \sin(2\Omega t + \theta)$$

A modulated laser light e (t) is given by Equation (1). The driver circuit for the optical modulator 131 belongs to the well known techniques and will not be explained.

$$e(t) = e^{i[\omega_0 t + \phi_1 \sin\Omega t + \phi_2 \sin(2\Omega t + \theta)]} \quad (1)$$
$$= e^{i\omega_0 t} \times e^{i\phi_1 \sin\Omega t} \times e^{i\phi_2 \sin(2\Omega t + \theta)}$$

$$e^{i\phi \sin\Omega t} = \sum_{m=-\infty}^{+\infty} J_m(\phi) e^{im\Omega t} \quad (2)$$

Jm($\phi$) is m order Bessel function $$e^{i\omega_0 t} \times e^{i\phi_1 \sin\Omega t} \times e^{i\phi_2 \sin(2\Omega t + \theta)} = e^{i\omega_0 t} \times \left[\sum_{m=-\infty}^{+\infty} J_m(\phi_1) e^{im\Omega t}\right] \times \quad (3)$$
$$\left[\sum_{n=-\infty}^{+\infty} J_n(\phi_2) e^{in(2\Omega t + \theta)}\right]$$
$$= e^{i\omega_0 t} \times$$
$$\left[\sum_{m=-\infty}^{+\infty} \sum_{n=-\infty}^{+\infty} J_m(\phi_1) J_n(\phi_2) e^{[i(m+2n)\Omega t + n\theta]}\right]$$
$$= e^{i\omega_0 t} \times \sum_{s=-\infty}^{+\infty} A_s e^{is\Omega t}$$

$$s = m + 2n,$$

$$A_s = \sum_{s=-\infty}^{+\infty} J_{s-2n}(\phi_1) J_{2n}(\phi_2) e^{in\theta}$$

Equation (3) represents that the center angular frequency of the frequency COMBs is $\omega_0$, and the frequency COMBs are distributed from the lower side to the higher side of the center angular frequency. θ can be regulated using a phase shifter (not shown) in order to obtain a flat and wide characteristics of the frequency COMBs.

Figure 2C:
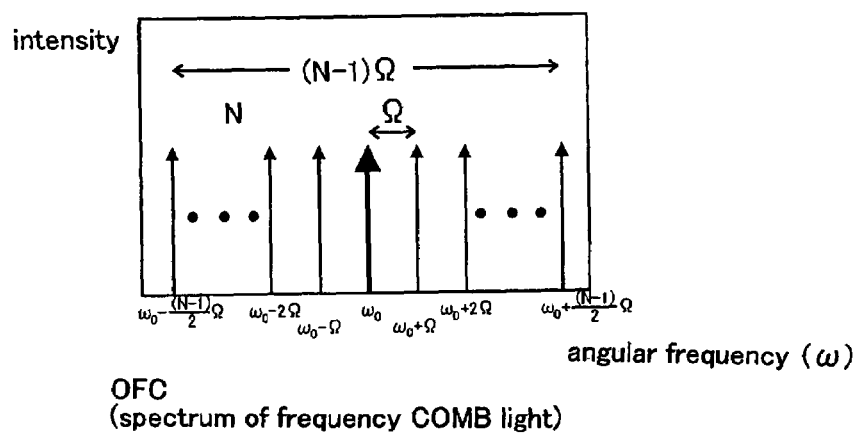

FIG. 2(C) represents the spectrum view of the Equation (3). FIG. 2(C) shows that N frequency COMBs with the frequency COMB angular frequency pitch (hereafter "COMB pitch") Ω are distributed in the bad of (N−1) Ω, where "N" is an odd number. The intensity of each frequency component is shown being uniform for sake of explanation. In actual the intensity of the frequency components is different, however it does not affect much the detection by the optical coherence tomography system.

Figure 3A:
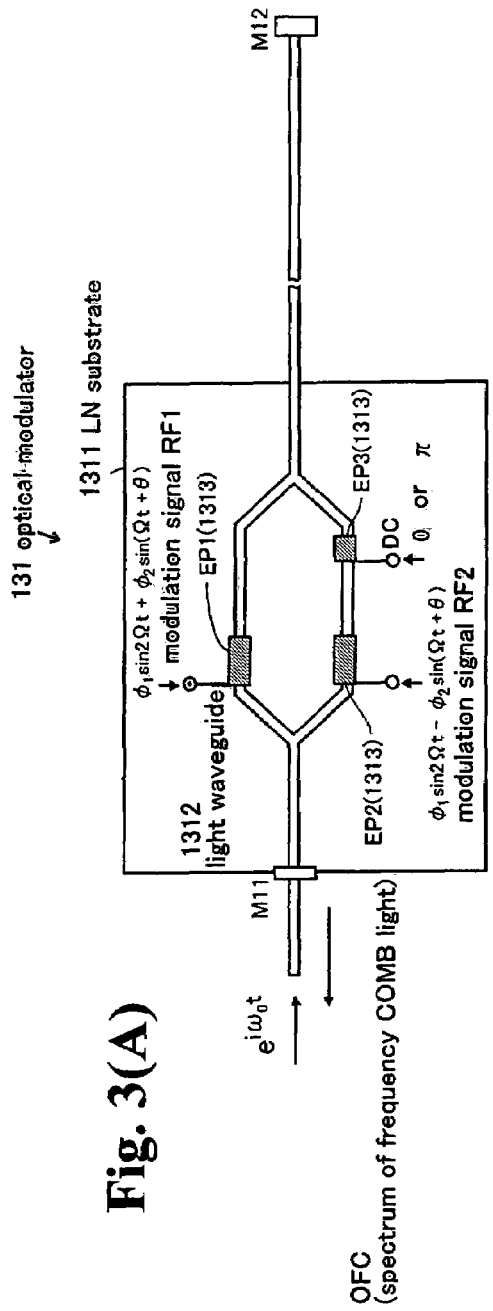
FIG. 3(A) shows a second example of an optical modulator in the frequency COMB light generator shown in FIG. 1; (B) shows a spectrum of the output light from the optical modulator shown in (A).

FIG. 3(A) shows a second example of the optical modulator 131. The optical modulator 131 in FIG. 3(A) is a Mach-Zehnder waveguide optical modulator, and a light waveguide 1312 and a modulation electrode 1313 are formed on the LN substrate 1311. The light waveguide 1312 is split into two light paths on the LN substrate 1311, and the modulation electrode 1313 is constituted of an electrode EP1 formed on one of the light paths (arm) and electrodes EP2 and EP3 formed on the other light path (arm).

In FIG. 3(A), the laser light (exp(iω$_0$t) is input in to the optical modulator 131, a modulation signal RF1 is fed to the electrode EP1, and a modulation signal RF2 is fed to the electrode EP2.

RF1=φ$_1$ sin Ωt+φ$_2$ sin(2Ωt+θ)

RF2=φ$_1$ sin Ωt−φ$_2$ sin(2Ωt+θ)

A bias DC is fed to the electrode EP3. The DC signal is applied to the bias DC such that the phase difference between the transmitted lights on the two optical paths is set to 0 or π.

When the signals are fed to the electrodes EP1, EP2, and EP3, respectively and the DC signal is applied to the bias DC for setting the phase difference between the transmitted lights on the two optical paths to 0 or π, the modulated laser light e(t) is given by Equation (4) using Bessel function.

$$E(t) = e^{i[\omega_0 t + \phi_1 \sin 2\Omega t + \phi_2 \sin(\Omega t + \theta)]} + \quad (4)$$
$$e^{i[\omega_0 t + \phi_1 \sin 2\Omega t - \phi_2 \sin(\Omega t + \theta) + \pi]}$$

$$= e^{i\omega_0 t}\sum_{p=-\infty}^{+\infty} J_p(\phi_1)e^{ip2\Omega t}\sum_{p=-\infty}^{+\infty} J_q(\phi_2)e^{iq(\Omega t+\theta)} -$$

$$e^{i\omega_0 t}\sum_{p=-\infty}^{+\infty} J_p(\phi_1)e^{ip2\Omega t}\sum_{p=-\infty}^{+\infty} (-1)^q J_q(\phi_2)e^{iq(\Omega t+\theta)}$$

$$= e^{i\omega_0 t}\sum_{p=-\infty}^{+\infty}\sum_{q=-\infty}^{+\infty} J_p(\phi_1)\{1-(-1)^q\}J_q(\phi_2)e^{i(2p+q)\Omega t}e^{iq\theta}$$

This equation is modified to Equation (5).

$$e^{i\omega_0 t}\sum_{s=-\infty}^{+\infty} e^{is(\Omega t+\theta)}\left[\sum_{p=-\infty}^{+\infty} \{1-(-1)^{s-2p}\}J_p(\phi_1)J_{s-2p}(\phi_2)e^{-i2p\theta}\right] = \quad (5)$$

$$e^{i\omega_0 t}\sum_{s=-\infty}^{+\infty}\{1-(-1)^{s-2p}\}A_s e^{is(\Omega t+\theta)}$$

$$s = 2p + q,$$

-continued $$A_s = \sum_{s=-\infty}^{+\infty} J_p(\phi_1)J_{s-2p}(\phi_2)e^{-i2p\theta}$$

Figure 3B:
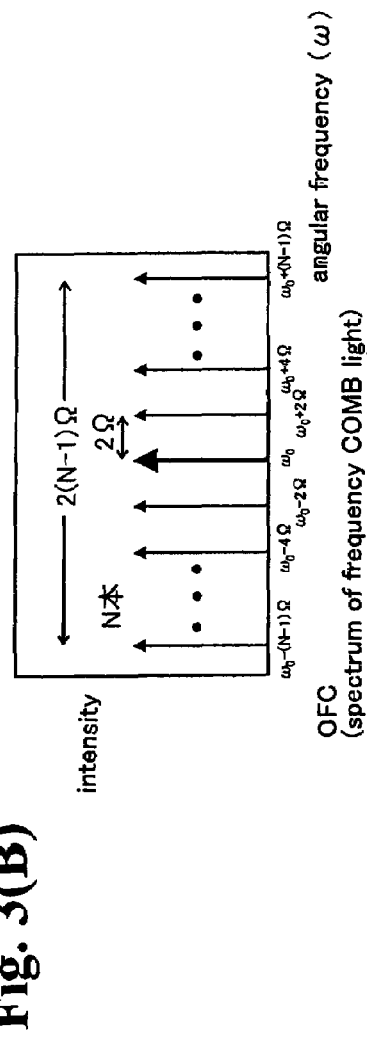

The terms in Equation (5) becomes zero when "s" is an even number. That is to say, Equation (5) represents the frequency COMBs constituted of only the odd-order terms. The frequency COMBs are distributed in both high frequency side and low frequency side of the center angular frequency ω$_0$ with the COMB pitch 2Ω as shown in FIG. 3(B). FIG. 3(B) shows that N frequency COMBs are distributed in the band of 2(N−1) Ω with the COMB pitch 2Ω, where "N" is an odd number. The intensity of each frequency component is shown being uniform for sake of explanation. As explained referring FIG. 2(C), even if the intensity of the frequency components are different, it does not affect much the detection by the optical coherence tomography system.

As shown in FIG. 3(B) and FIG. 2(C), the COMB pitch and the band of the optical modulator 131 in FIG. 3(A) are double of those of the optical modulator 131 in FIG. 2(A).

Figure 4:
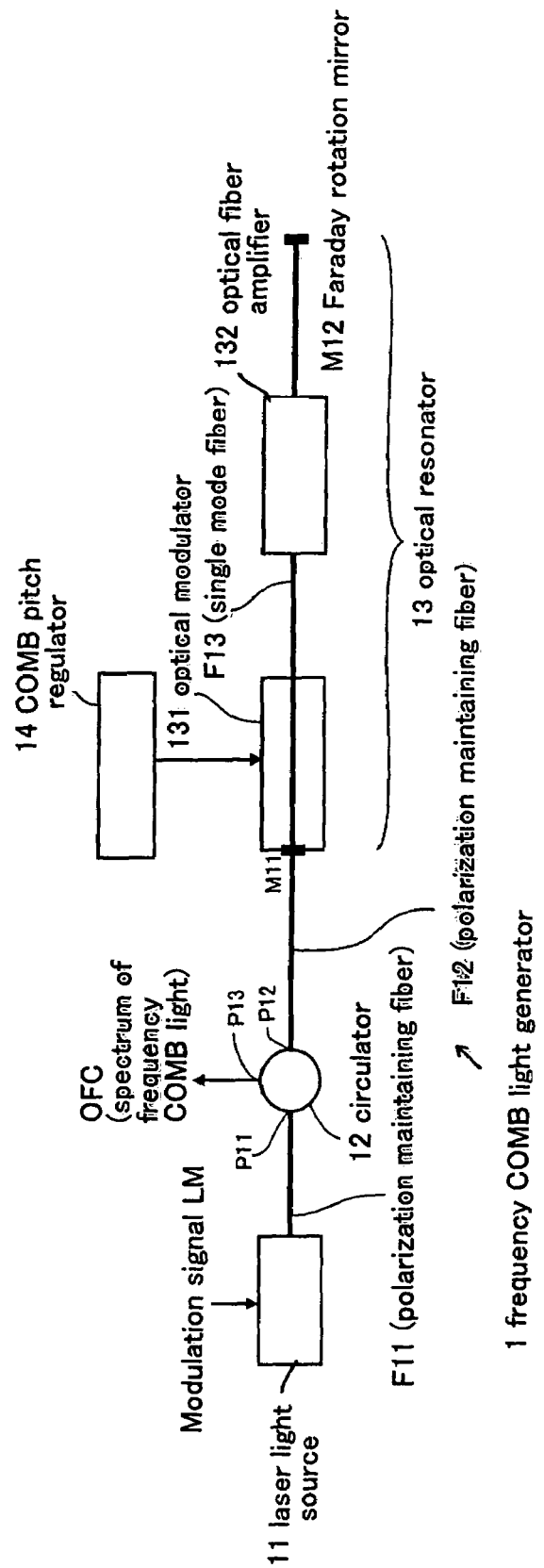
FIG. 4 shows an example of the frequency COMB light generator shown in FIG. 1 with an optical fiber amplifier.

When the light intensity between the first mirror M11 and the second mirror M12 attenuates in the frequency COMB light generator 1 shown in FIG. 1, an optical fiber amplifier 132 can be inserted between the first mirror M11 and the second mirror M12 on the optical fiber F13 as shown in FIG. 4.

Figure 5:
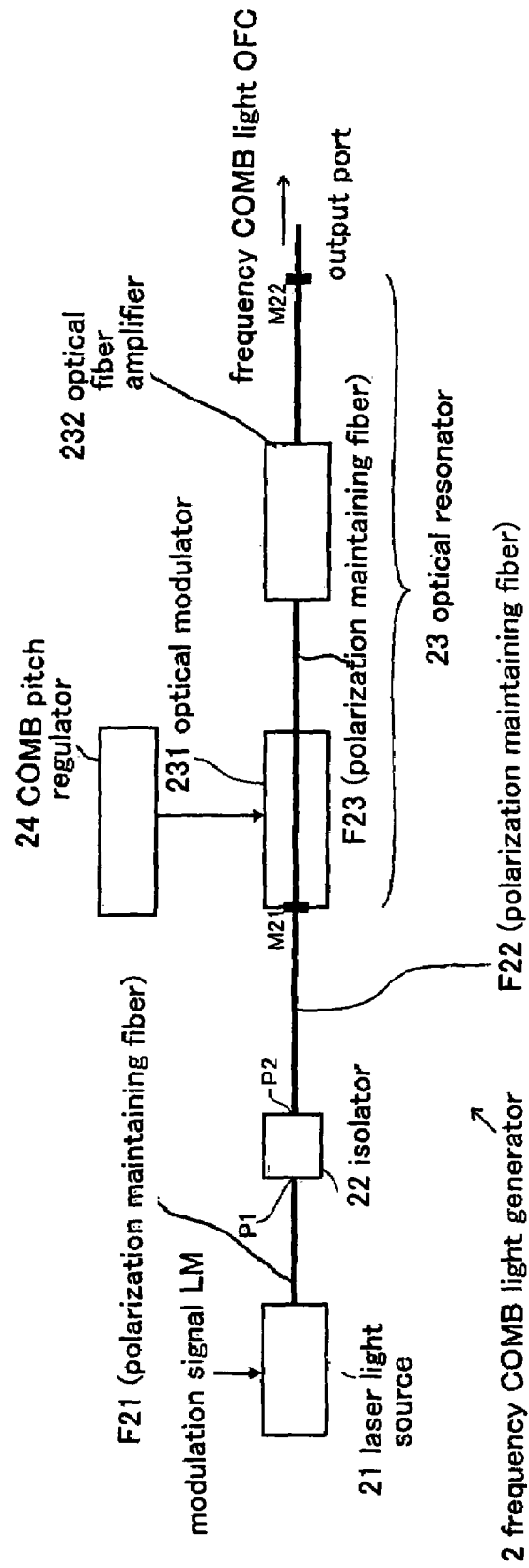
FIG. 5 shows a second embodiment of a frequency COMB light generator according to the present invention.

FIG. 5 shows a second embodiment of the frequency COMB light generator according to the present invention. In FIG. 5, the frequency COMB light generator 2 includes a laser light source 21, an isolator 22, an optical resonator 23 and a COMB pitch regulator 24.

The laser light source 21 can output the laser light (center angular frequency ω$_0$) in a wavelength band where the penetration efficiency in a living body is as high as the laser light source 21 in the first embodiment.

The isolator 22 is located between the laser light source 21 and the optical resonator 23, and the laser light source 21 is connected to a first port P21 through an optical fiber F21 (polarization maintaining fiber) and the optical resonator 23 is connected to a second port P22 through an optical fiber F22 (polarization maintaining fiber).

The optical resonator 23 generates the frequency COMB light OFC based on the laser light (center frequency ω$_0$) that is output from the laser light source 21. The optical resonator 23 includes an optical modulator 231, a first mirror M21, a second mirror M22 and an optical fiber amplifier 232.

The COMB pitch regulator 14 is a modulation signal generator for varying a modulation signal fed to the modulation electrode of the optical resonator 23, and the angular frequency pitch Ω can be varied or swept by varying the modulation frequency.

The first mirror M21 is located at one side of the optical modulator 231 where the isolator 22 is situated, and the second mirror M22 is connected to the other side of the optical modulator 231 through a length L of the optical fiber F23 (polarization maintaining fiber).

In this embodiment, the optical fiber amplifier 232 is a polarization maintaining fiber amplifier. The second mirror M22 is an output port of the frequency COMB light OFC.

The length of the optical fiber F23 is set such that the distance L between the first mirror M21 and the second mirror M22 becomes integral multiple (m) of a half of the wave length ($\lambda/2$). L is give by the following equation, where "n" is the refractive index of the optical fiber F23 and "c" is the light speed.

$$L = m \times (\lambda/2) \times (1/n) = (m/n) \times (c\pi/\omega_0)$$

The optical modulator 231 can have a configuration that is similar to that of the optical modulator 131 shown in FIG. 2(A) and FIG. 3(A).

Figure 6A:
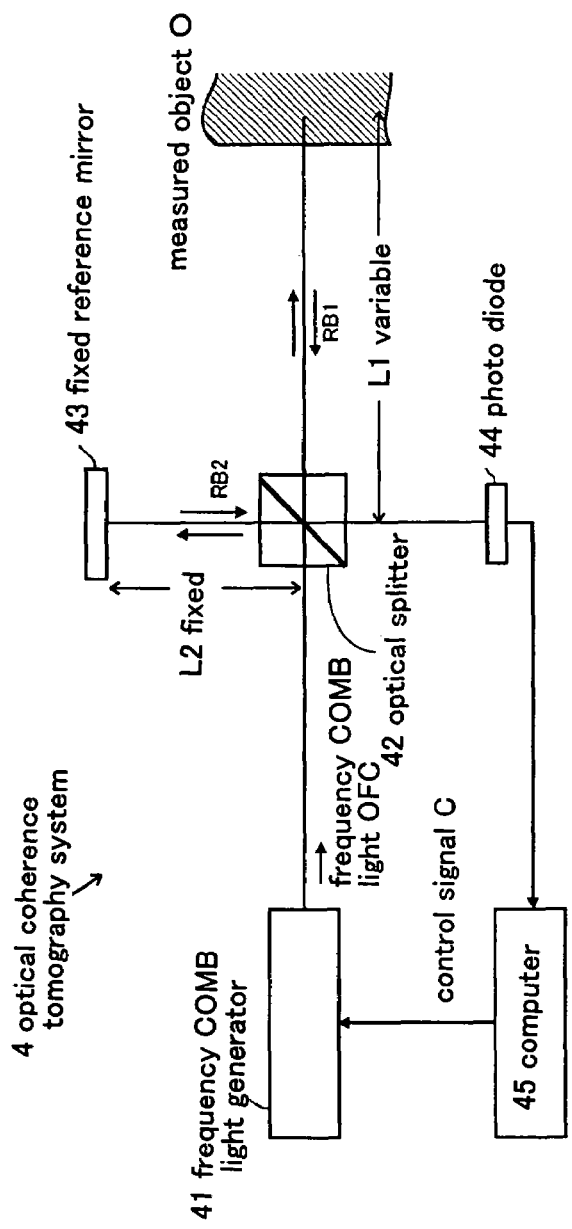
FIG. 6(A) shows a basic configuration of an optical coherence tomography system according to the present invention; (B) shows a spectrum of the output light from the frequency COMB light generator shown in (A).

An optical coherence tomography system as the basic configuration of the shape measurement apparatus according to the present invention will be explained referring to FIG. 6(A), (B) and FIG. 7. In FIG. 6(A), the optical coherence tomography system 4 includes a frequency COMB light generator 41, an optical splitter 42, a fixed reference mirror 43 and a photo diode 44 that functions as an optical detector, and constitutes an optical interferometer.

The frequency COMB light generator 1 shown in FIG. 1 and FIG. 4 and the frequency COMB light generator 2 shown in FIG. 5 can be used as the frequency COMB light generator 41. The frequency COMB light generator 41 is controlled by a control signal C from a computer 45.

Figure 11A:
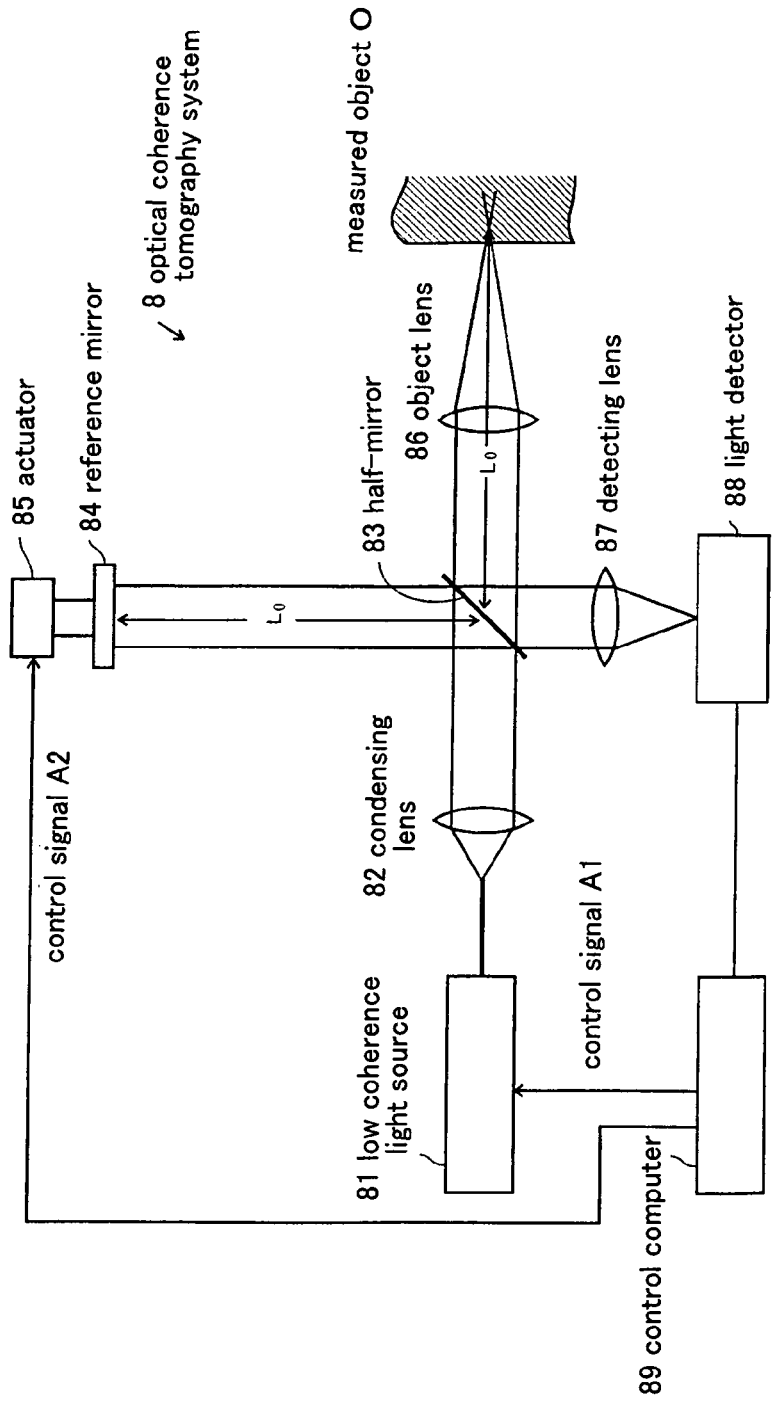
FIG. 11(A) shows a prior art optical coherent tomography system; (B) shows the frequency spectrum of a low coherence light source.
Figure 11B:
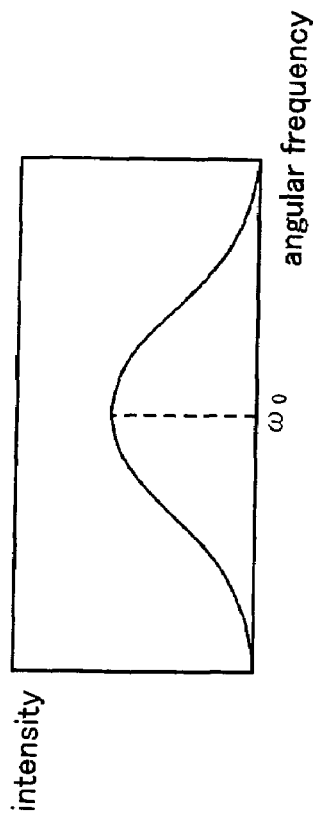
Figure 12A:
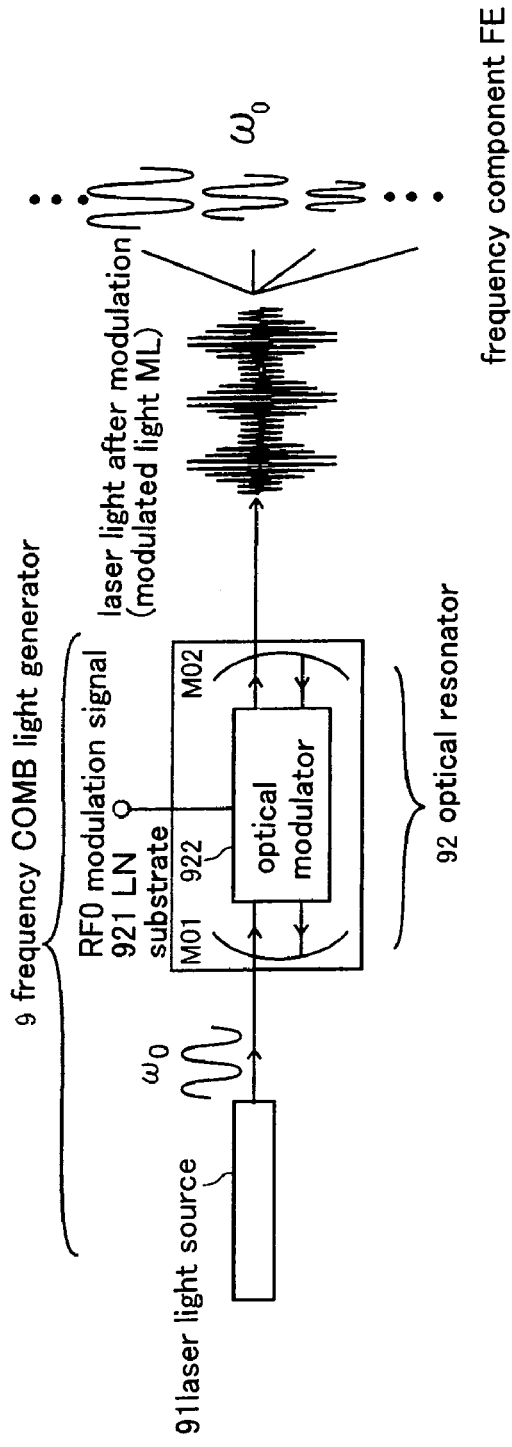
FIG. 12(A) shows a prior art frequency COMB light generator; (B) shows the frequency spectrum of the prior art frequency COMB light generator.
Figure 12B:
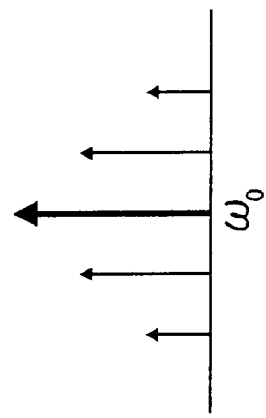

Although the reference mirror is movable in the conventional optical interferometer (see the reference mirror 84 in FIG. 11), the reference mirror in the present invention is fixed (the fixed reference mirror 84 in FIG. 11).

The optical splitter 42 (shown as a half-mirror in FIG. 6(A)) splits the output light of the frequency COMB light generator 41 (frequency COMB light OFC) into two parts, outputs one part to the fixed reference mirror 43 and outputs the other part toward the measured object O.

The optical splitter 42 outputs multiplexes the reflected light RB1 from the measured object O and the reflected light RB2 from the fixed reference mirror 43 and outputs to the photo diode 44. The frequency COMB light generator 41 varies the COMB pitch and regulates the observation depth of the measured object O by varying the fed modulation signal (see RF in FIG. 2(A), (B), RF1, RF2 in FIG. 3(A)).

The operation of the optical coherence tomography system 4 will be explained in detail hereafter. As shown in the spectrum in FIG. 6(B), the frequency COMB light OFC has N frequency COMBs that are distributed in the band of (N−1)Ω with the COMB pitch of Ω, where "N" is an odd number. The center angular frequency is $\omega_0$, (N−1)/2 frequency COMBs are positioned at the higher frequency side and the lower frequency side respectively. This distribution is similar to that shown in FIG. 2(C).

Figure 6B:
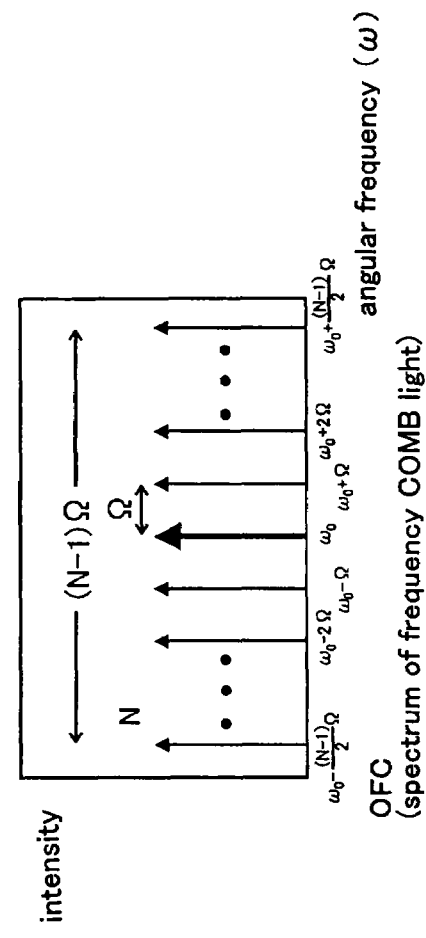

In the spectrum shown in FIG. 6(B), the intensity of each frequency component is shown being uniform for sake of explanation. In actual the intensity of the frequency components is different, however it does not affect much the detection by the photo diode 44.

The electric field e(t) of the frequency COMB light generator 41 is represented by Equation (6).

$$e(t) = e^{i\left[(\omega_0 - \frac{(N-1)}{2}\Omega)t + \phi_{-\frac{(N-1)}{2}}\right]} \ldots + \tag{6}$$
$$e^{i[(\omega_0 - \Omega)t + \phi_{-1}]} + e^{i[\omega_0 t + \phi_0]} + e^{i[(\omega_0 - \Omega)t + \phi_1]} \ldots +$$
$$e^{i\left[(\omega_0 \frac{(N-1)}{2}\Omega)t + \phi_{\frac{(N-1)}{2}}\right]}$$
$$= e^{i\omega_0} \sum_{m=-\frac{(N-1)}{2}}^{\frac{(N-1)}{2}} e^{i(m\Omega t + \phi_m)}$$

$\tau_1$ is the time while the output light of the frequency COMB light generator 41 (frequency COMB light OFC) passes through the optical splitter 42 and is reflected at the measured object O, then at the optical splitter 42, and finally arrives at the photo diode 44. The path where the frequency COMB light OFC is reflected at the measured object O and arrives at the photo diode 44 is called "a first path pth$_1$".

$\tau_2$ is the time while the output light of the frequency COMB light generator 41 (frequency COMB light OFC) is reflected at the optical splitter 42, then at the fixed reference mirror 43, and passes through the optical splitter 42 and is reflected at the measured object O, then at the optical splitter 42, passes through the optical splitter 42 and arrives at the photo diode 44. The path where the frequency COMB light OFC is reflected at the fixed reference mirror 43 and arrives at the photo diode 44 is called "a second path pth$_2$".

The light "$e_1(t)$" on the first path "pth$_1$" immediately before the photo diode 44 is expressed by Equation (7).

$$e_1(t) = \alpha e(t - \tau_1) = \alpha e^{i\omega_0} \sum_{m=-\frac{(N-1)}{2}}^{\frac{(N-1)}{2}} e^{i(m\Omega(t-\tau_1)+\phi_m)} \tag{7}$$

The light "$e_2(t)$" on the second path "pth$_2$" immediately before the photo diode 44 is expressed by Equation (8).

$$e_2(t) = \beta e(t - \tau_2) = \beta e^{i\omega_0} \sum_{m=-\frac{(N-1)}{2}}^{\frac{(N-1)}{2}} e^{i(m\Omega(t-\tau_2)+\phi_m)} \tag{8}$$

$\alpha$ in Equation (7) and $\beta$ in Equation (8) are the fractions of the light on the first path and the second path.

The optical current that passes through the photo diode 44 is in proportion to the light intensity:

$$|e_1(t) + e_2(t)|^2$$

The response rate of the photo diode 44 used here is slow. That is to say, the photo diode 44 does not respond to the angular frequency of the frequency COMB light OFC. The output of the photo diode 44 is a time average of $|e_1(t) + e_2(t)|^2$ and results in $\langle |e_1(t) + e_2(t)|^2 \rangle$.

"$\langle\ \rangle$" here represents a time average. This time average is expressed by Equation (9).

$$\langle |e_1(t) + e_2(t)|^2 \rangle = \langle |e_1(t)|^2 + |e_2(t)|^2 + e_1(t)_2 e^*(t) + e_1^*(t)e_2(t) \rangle = \tag{9}$$
$$\alpha^2 \langle |e(t - \tau_1)|^2 \rangle + \beta^2 \langle |e(t - \tau_2)|^2 \rangle + \alpha\beta \langle e(t - \tau_1)e^*(t - \tau_2) \rangle +$$
$$\alpha\beta \langle e^*(t - \tau_1)e(t - \tau_2) \rangle = (\alpha^2 + \beta^2)N +$$
$$\alpha\beta \text{Re}\left[ e^{i\omega_0(\tau_1-\tau_2)} \sum_{m=-\frac{(N-1)}{2}}^{\frac{(N-1)}{2}} e^{i\Omega(\tau_1-\tau_2)} \right] =$$
$$(\alpha^2 + \beta^2)N + 2\alpha\beta\cos\left[\omega_0 + \frac{N}{2}\Omega\right)\tau\right]\frac{\sin\left[\frac{(N+1)\Omega\tau}{2}\right]}{\sin\left(\frac{\Omega\tau}{2}\right)}$$

-continued $$\tau = \tau_1 - \tau_2 = \frac{2n}{c}(L_1 - L_2),$$

"n" represents the refraction index of the light path medium", and "c" represents the light speed.

Figure 7:
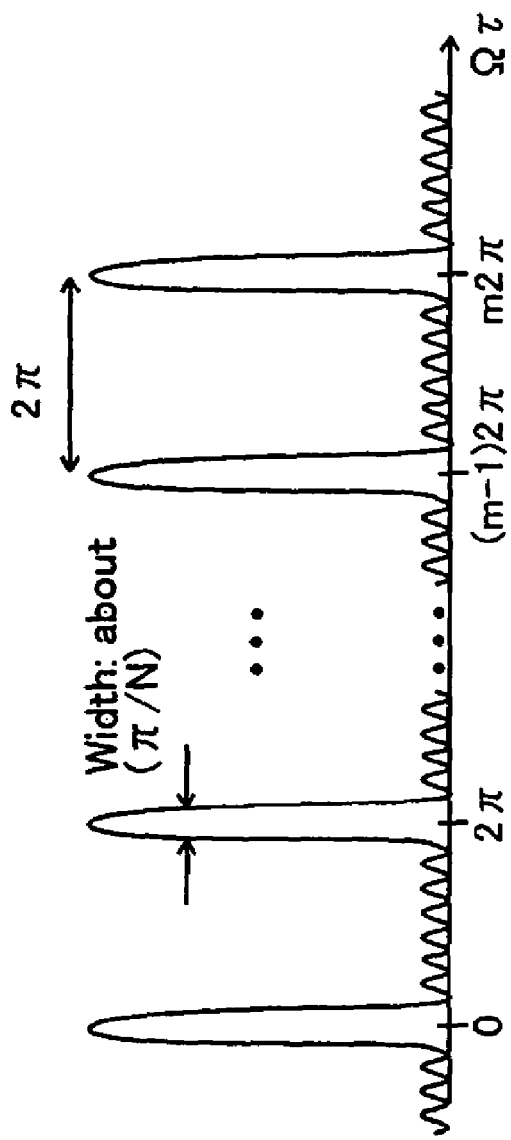
FIG. 7 shows a detailed spectrum of the output light from the light source for explanation of the operation of the frequency COMB light generator shown in FIG. 6(A).

The form of the second term in the most right-hand side of Equation (9):

$$f(0) = \frac{\sin\left[\frac{(N+1)\Omega\tau}{2}\right]}{\sin\left(\frac{\Omega\tau}{2}\right)} \quad (10)$$

has a sharp peak at every integral multiple of $2\pi$ as shown in FIG. 7, where the variable number is $\Omega\pi$. The larger N becomes, the sharper the peak becomes.

L1 is the light path length from the optical splitter 42 to the reflection point in the measured object O (the point where the frequency COMB light OFC is reflected inside the measured object O). L2 is the light path length from the optical splitter 42 to the fixed reference mirror 43.

When a m order peak interference is observed by the photo diode 44, L' is expressed by Equation (11) assuming $L_1-L_2=L'$ from the condition of $\Omega\tau=\Omega(2n/c)(L_1-L_2)=2$ m$\pi$.

$$L' = \frac{c}{2n\,\nu_{RF}} \times m \quad (11)$$

"m" represents an integer number, "$\nu_{RF}$" is the frequency pitch ($2\pi\nu_{RF}=\Omega$) of the frequency COMB light.

The frequency pitch $\nu_{RF}$ (or COMB pitch $\Omega$) of the frequency COMB light OFC can be varied by the modulation signal (see RF in FIG. 2(A), (B) and RF1, RF2 in FIG. 3(A)). When $\nu_{RF}$ (or COMB pitch $\Omega$) is gradually varied, the interference position changes accordingly.

The spatial resolution r corresponds to the peak sharpness, and is expressed by Equation (12).

$$r \simeq \frac{c}{2n\nu_{RF}} \times \frac{1}{N} \quad (12)$$

When $\nu_{RF}$ is varied by $\Delta\nu$, the change in the interference position $\Delta L'$ is expressed by:

$$\Delta L' = L' \times (\Delta\nu/\nu_{RF})$$

For example, when $\nu_0=200$ THz ($\omega_0=2\pi\nu_0$, the wave length of the light is 1.3 µm), $\nu_{RF}=10$ GHz and N=700, the band of the frequency COMB light OFC becomes N×$\nu_{RF}$=7 THz (wave length band: 53 nm) When "n" (refraction index)=1, and "m" (order of the interference)=1, L' (=L1−L2)=15 mm, and r (spatial resolution)=21 µm. When $\nu_{RF}$ is varied in the range e.g. from 8 GHz to 12 GHz by the step of 1 MHz, $\Delta L'$ becomes about 6 mm and therefore the measured object O can be measured to the depth of 6 mm with the resolution of 15 µm.

A first embodiment of a shape measurement apparatus (a optical coherence tomography system) according to the present invention will be explained referring to FIG. 8. The optical coherence tomography system 5 in FIG. 8 realizes the optical coherence tomography system in FIG. 6(A) by a spatial interference system, and includes a frequency COMB light generator 51, a condensing lens 52, a half mirror 53, a variable focal point lens 54, a fixed reference mirror 55, a detection lens 56, an optical detector 57, an imaging sensor 58 and a computer 59. In this embodiment, the half mirror 53 is used as an optical splitter.

The frequency COMB light generator 51 can use the frequency COMB light generator 1 shown in FIG. 1 and FIG. 4, the frequency COMB light generator 2 shown in FIG. 5, or the frequency COMB light generator 7 shown in FIG. 10 that will be explained later.

The frequency COMB light OFC output from the frequency COMB light generator 51 is collimated by the condensing lens 52 and output to the half mirror 53. The half mirror 53 splits the input light from the condensing lens 52 into two parts. One part is output toward the measured object O through the variable focal point lens 54 and the other part is output to the fixed reference mirror 55.

The half mirror 53 multiplexes the reflected light RB1 from a reflection point in the measured object O (a point reflecting the frequency COMB light OFC inside the measured object O) and the reflected light RB2 from the fixed reference mirror 55 and outputs to the optical detector 57 and the imaging sensor 58. The frequency COMB light generator 51 is controlled by the control signal C1 from the computer 59, and the variable focal point lens 54 is controlled by the control signal C2 from the computer 59

The optical detector 57 (similar to the optical coherence tomography system 4 in FIG. 6(A)) detects the interference between the light on the path (the first path "pth$_1$") where the output light from the frequency COMB light generator 51 (frequency COMB light OFC) is reflected at the measured object O and arrives at the imaging sensor 58 and the light on the path (the second path "pth$_2$") where the output light from the frequency COMB light generator 51 is reflected at the fixed reference mirror 55 and arrives at the imaging sensor 58. The imaging sensor 58 detects the light from the first path "pth$_1$" by the imaging sensor 58.

L1 is the light path length from the half mirror 53 to the reflection point in the measured object O (the point reflecting the frequency COMB light OFC inside the measured object O), and L2 is the light path length from the half mirror 53 to the fixed reference mirror 55.

When the frequency COMB light OFC is input into the imaging sensor 58 and the light path difference L'=L1−L2 becomes a particular value, i.e. an integer (m) multiple of ($\pi$ c/n $\Omega$), a very high value of the interference is observed.

Since this distance difference is in inverse proportion to the COMB pitch $\Omega$, the interference by the reflected light from a point inside the measured object O can be detected by controlling the COMB pitch $\Omega$ by the computer 59 (by varying the modulation signal RF). At this time, the focal point of the variable focal point lens 54 is controlled in synchronization with the scan of the COMB pitch $\Omega$.

Since the optical coherence tomography 5 according to this embodiment has no movable portion, a low production cost and a high reproducibility are achieved. The tomographic image data are obtained by the imaging sensor 58 and displayed on the display screen (not shown) of the computer 59.

A second embodiment of a shape measurement apparatus (a optical coherence tomography system) according to the present invention will be explained referring to FIG. 9. The optical coherence tomography system 6 in FIG. 9 realizes the optical coherence tomography system by an optical fiber, and includes a frequency COMB light generator 61, an optical fiber splitter 62, a probe lens 63, a fixed reference mirror 64, a detection lens 65, an optical detector 66 and computer 67. In this embodiment, an avalanche photo diode can be used as the optical detector 66.

The frequency COMB light generator 61 is controlled by the control signal C from the computer 67. The frequency COMB light OFC output from the frequency COMB light generator 61 transmits through an optical fiber F6 and is split into two parts at the optical fiber splitter 62. One part is reflected by the fixed reference mirror 64 at the end of the optical fiber F6 (polarization maintaining fiber) and converted to the light transmitted toward the detection lens 65 through the optical fiber F6 by the optical splitter 62. This converted light is fed to the optical detector 66 through the detection lens 65.

The other part of the split light by the optical fiber splitter 62 is output toward the measured object O through the probe lens 63. The reflected light from the measured object O is input into the optical fiber F6 and input into the optical detector 66 through the detection lens 65.

Figure 8:
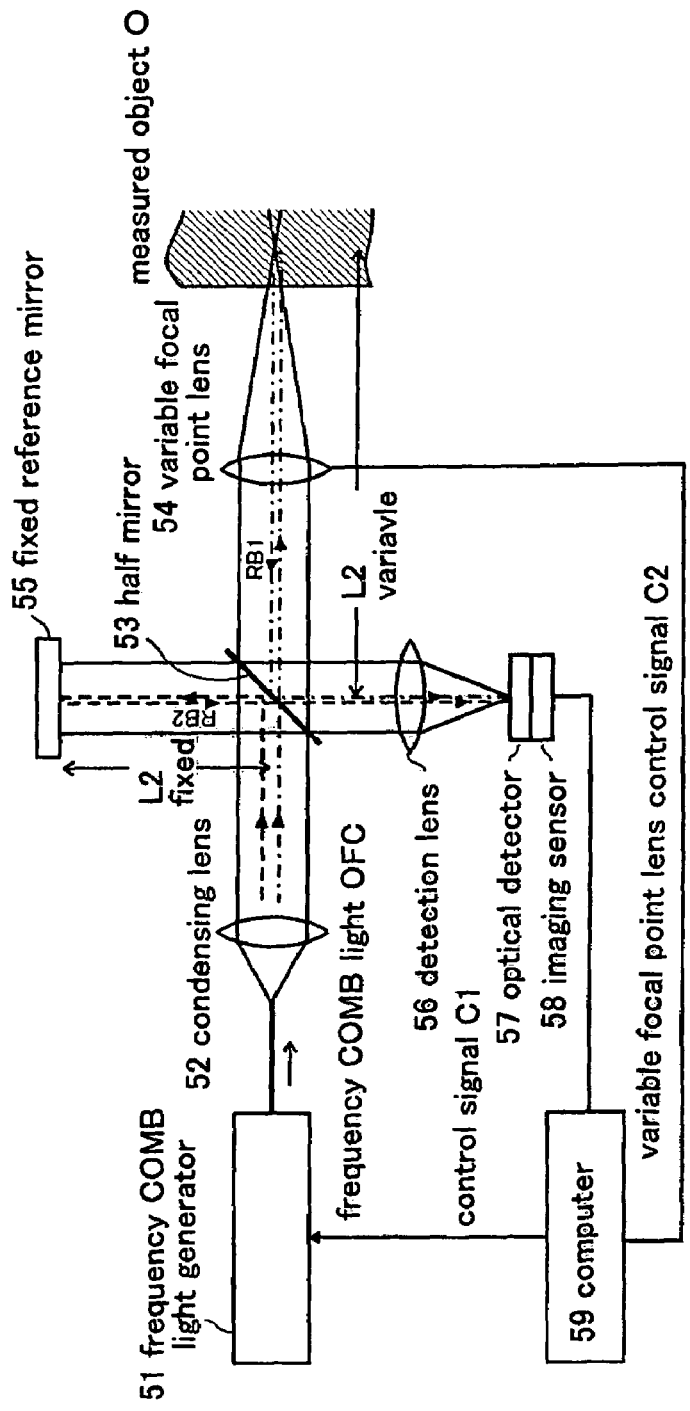
FIG. 8 shows a first embodiment of an optical coherence tomography system according to the present invention.
Figure 9:
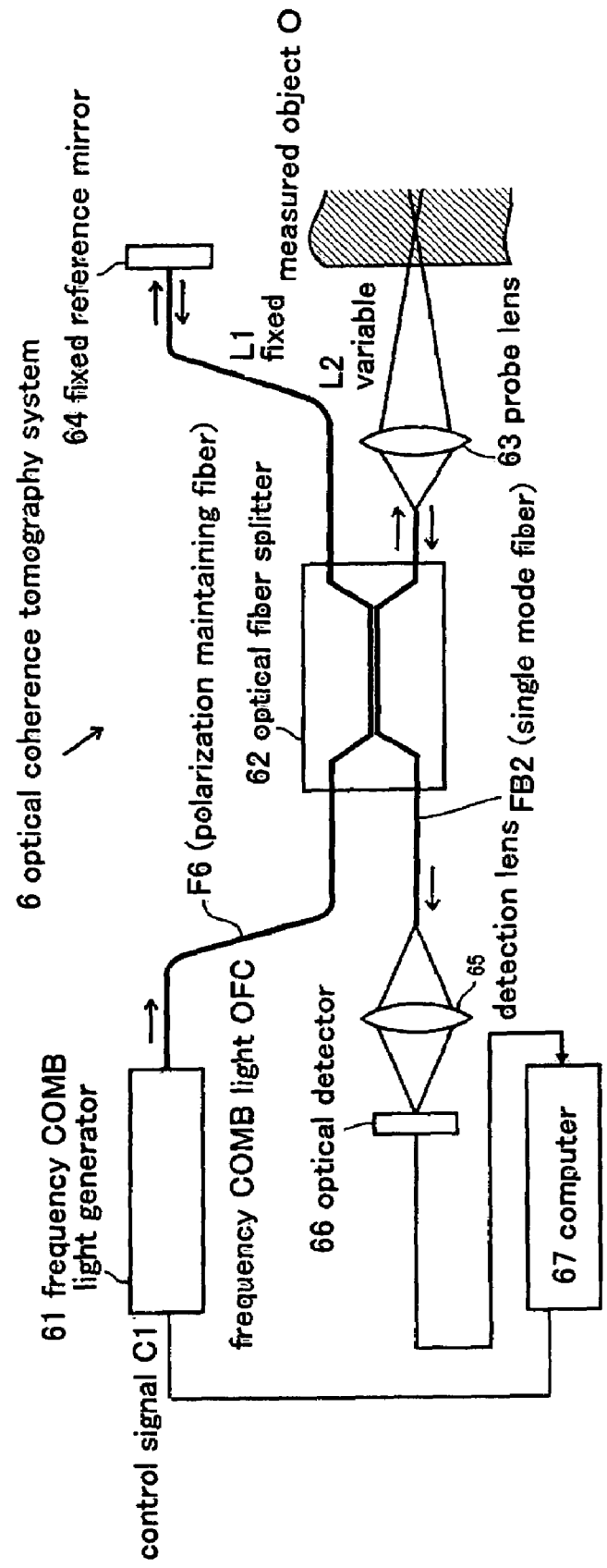
FIG. 9 shows a second embodiment of an optical coherence tomography system according to the present invention.

The operation of the optical coherence tomography system 6 in FIG. 9 is basically same as that of the optical coherence tomography system 4 in FIG. 6(A) and the optical coherence tomography system 5 in FIG. 8.

Figure 10:
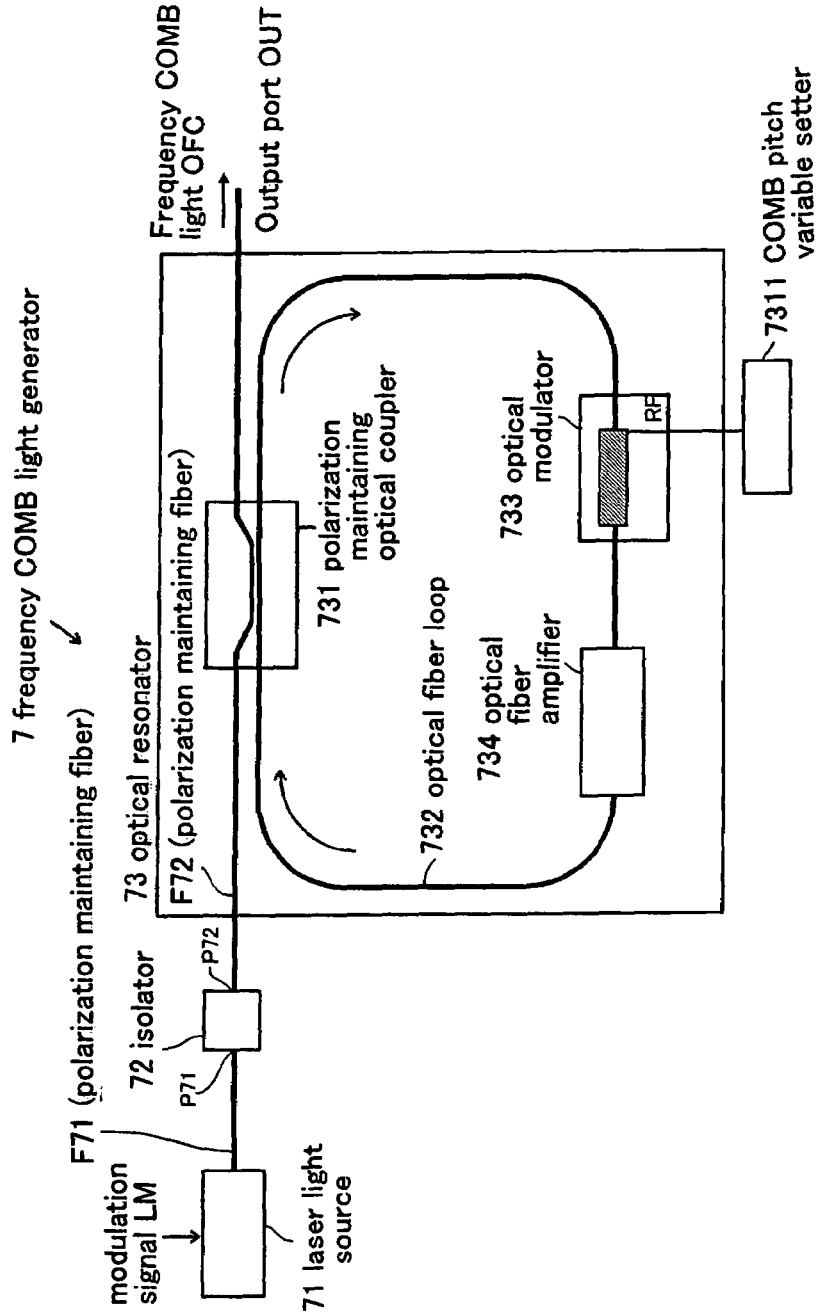
FIG. 10 shows a single loop frequency COMB light generator which can be used as the frequency COMB light generator in the optical coherent tomography system shown in FIG. 6 and FIG. 9.

FIG. 10 shows a frequency COMB light generator that can be used in the above mentioned optical coherence tomography system. In FIG. 10, the frequency COMB light generator 7 includes a laser light source 71, an isolator 72 and an optical resonator 73.

The laser light source 71 can output a laser light (center angular frequency $\omega_0$) having a wavelength band where the penetration efficiency in a living body is high, and the center frequency $\omega_0$ of the output light can have a width by inputting the modulation signal LM.

The isolator 72 is located between the laser light source 71 and the optical resonator 73, and the laser light source 71 is connected to a first port P71 through an optical fiber F71 and the optical resonator 73 is connected to a second port P72 through an optical fiber F72 (polarization maintaining fiber).

The laser light source 71 can output a laser light (center angular frequency $\omega_0$) having a wavelength band (e.g. 1.2~1.6 μm) where the penetration efficiency in a living body is high, and the center frequency $\omega_0$ of the output light can have a width by inputting the modulation signal LM in a manner that is similar to that for the laser light source 11 in FIG. 1 and FIG. 4 and the laser light source 21 in FIG. 5.

The isolator 72 is located between the laser light source 71 and the optical resonator 73, and the laser light source 71 is connected to a first port P71 through an optical fiber F71 (polarization maintaining fiber) and the optical resonator 73 is connected to a second port P72 through an optical fiber F72 (polarization maintaining fiber).

The optical resonator 73 generates the frequency COMB light OFC based on the laser light (center frequency $\omega_0$) that is output from the laser light source 71. The optical resonator 73 includes a polarization maintaining optical coupler 731, an optical fiber loop 732, an optical modulator 732 that has the same configuration as the optical modulator 131 in FIG. 2(A), (B) and an optical fiber amplifier 734.

Part of the output light (angular frequency $\omega_0$) is input into the optical fiber loop 732 at the polarization maintaining optical coupler 731. Part of the light that is input into the optical fiber loop 732 is shifted for the modulation frequency by the COMB pitch Ω at the optical modulator 733 and results in the light of the angular frequency ($\omega_0 \pm \Omega$). This light returns to the polarization maintaining optical coupler 731 after going around the optical fiber loop 732, and goes abound the optical fiber loop 732 again. Part of the light of the angular frequency ($\omega_0 \pm \Omega$) is frequency shifted by the optical modulator 733, and results in the light of the angular frequency ($\omega_0 \pm 2\Omega$).

In this embodiment, since the optical fiber amplifier 734 compensates the optical loss in the optical fiber loop 732, the light going around the optical fiber loop 732 will not become weak.

Accordingly, since the continuous light is always emitting from the laser light source 71, the laser light having N frequency COMBs of $\{\omega_0-(N-1)\Omega/2, \ldots, \omega_0-2\Omega, \omega_0-\Omega, \omega_0, \omega_0+\Omega, \omega_0+2\Omega, \ldots, \omega_0+(N-1)\Omega/2\}$ is output form the output port OUT by having the input light to the polarization maintaining optical coupler 731 go around the optical fiber loop 732. The laser light is the frequency COMB light OFC in which N frequency COMBs with the COMB pitch Ω is distributed in the band of $(N-1)\Omega$ (see FIG. 2(C)), where N is an odd number.

INDUSTRIAL APPLICABILITY (1) The method for measuring a shape and the apparatus according to the present invention for measuring a shape such as an optical coherence tomography system uses frequency COMBs as the light and achieves the following effects.

(a) In a typical conventional optical coherence tomography, plural mechanical movable portions are required. However when the method shape and the apparatus for measuring a according to the present invention is applied to an optical coherence tomography system, at least a reference mirror is fixed. Therefore a small size optical coherence tomography system with high reproducibility and high quake resistance can be realized.

(b) When the method and the apparatus for measuring a shape according to the present invention is applied to an optical coherence tomography system, since the strength of the frequency COMB light generated by the frequency COMB light generator is much higher than that of the light generated by the conventional low coherence light source, the utilization efficiency of the light becomes higher and it enables an observation of the deep portion at a high accuracy that has been impossible by the conventional optical coherence tomography. When the method and the apparatus for measuring a shape according to the present invention is applied to an optical coherence tomography system, since the frequency COMB light generator is used in place of the low coherence light source (see numerical number 81 in FIG. 11(A)) and the frequency pitch of the frequency COMBs is made variable, an observation under a skin to a deep portion and at a high depth spatial resolution becomes possible.

(c) In the method for measuring a shape and the apparatus according to the present invention, an imaging sensor can be used and it allows a shorter measurement time and the shape measurement of a moving object.

(d) In the method for measuring a shape and the apparatus according to the present invention, since a lot of frequency COMBs can be generated, a high depth spatial resolution is achieved. For example, the depth spatial resolution was about 10 μm in the conventional optical coherence tomography system. When the apparatus for measuring a shape according to the present invention is applicable to an optical coherence tomography system, light COMBs in the bandwidth of about 100 nm can be generated for the laser light of 1.3 μm center wavelength and therefore the depth spatial resolution can be improved to 5 μm.

(e) As mentioned above, the performance of the method and the apparatus for measuring a shape according to the present invention is significantly improved. When they are applicable to an optical coherence tomography system, the various problems in clinical medicine fields (large side, expensive, etc.) can be resolved. The method and the apparatus for measuring a shape according to the present invention are applicable to not only an optical coherence tomography system but also general apparatuses for measuring microscopic shapes.

(2) In the frequency COMB light generator according to the present invention, the distance between mirrors in an optical resonator can be enough long by using an optical fiber. Therefore, the resonance frequency pitch becomes small and the frequency pitch of the frequency COMBs can be variable. It is possible to compensate the effect of a change in the polarization condition of an optical fiber by using a Faraday rotation mirror as one of two reflection mirrors. It is also possible to make the polarization condition unchanged by using a polarization maintaining fiber as the optical fiber that is drown out from the resonator. Since a fiber amplifier is used when necessary in the frequency COMB light generator according to the present invention, the reflected light (signal light) from inside of an object with strong dispersion can be detected at a high SN ratio.

The invention claimed is:

1. A method for shape measurement comprising the steps of:
generating a frequency COMB light by inputting a laser light from a laser light source into an optical fiber which compensates a change in the polarization condition and maintains the polarization, and has a first mirror and a second mirror which are positioned with a resonant distance in between and modulating the laser light transmitting between the first mirror and the second mirror using a modulation electrode; and
measuring a shape of an measured object using an optical interferometer by inputting the frequency COMB light into the optical interferometer for distance measurement, wherein further comprising the step of:
regulating an observation depth by varying the modulation signal applied to the modulation electrode so that a frequency pitch of frequency COMBs which constitutes the frequency COMB light is varied.

2. A method for shape measurement of claim 1 wherein, the optical interferometer performs a light detection by splitting the frequency COMB light into two parts using an optical splitter, outputting one part to a fixed reference mirror, outputting the other part toward the measured object, and combining the light reflected from the fixed reference mirror and the light reflected from the measured object using the optical splitter.

3. A method for shape measurement of claim 2 wherein, the frequency COMB light combined by the optical splitter is detected by an image sensor which functions as the optical detector or an image sensor which is positioned separate from the optical detector, and the focal point of the frequency COMB light which is output toward the measured object is regulated by a variable focal point lens positioned between the optical splitter and the measured object.

4. An apparatus for shape measurement comprising:
a frequency comb light generator including:
a laser light source;
an optical resonator for generating a frequency COMB light from the laser light which is output by the laser light source;
a COMB pitch regulator for varying the frequency pitch of a frequency COMBs which constitutes the frequency COMB light; and
an output port for outputting a resonant output from the optical resonator; and
an optical interferometer for measuring the distance which uses the frequency COMB light generator as a light source, wherein
the optical resonator includes:
an optical modulator for modulating the light by a modulation electrode;
a first mirror which is positioned at one end of a light waveguide of the optical modulator;
an optical fiber which is drawn out form the other end of the waveguide of the optical modulator;
a second mirror which is positioned at the end of optical fiber,
the COMB pitch regulator is a modulation signal generator for varying the modulation signal which is fed to the modulation electrode, and
the second mirror is an apparatus for compensating the change in the polarization condition, or
the optical fiber is a polarization maintaining fiber.

5. An apparatus for shape measurement of claim 4, wherein the optical interferometer comprises an optical splitter, a fixed reference mirror and an optical detector, the frequency COMB light from the frequency comb light generator is split into two parts by the optical splitter, one part is output to the fixed reference mirror, the other part is output to the measured object, the reflected light from the fixed reference mirror is combined with the reflected light from the measured object by the optical splitter, and the combined light is output to the optical detector.

6. An apparatus for shape measurement of claim 5 wherein, the optical interferometer is a spatial optical system and the optical splitter is a half mirror, or the optical interferometer is an optical fiber system and the optical splitter is an optical fiber splitter.

7. An apparatus for shape measurement of claim 6 wherein, the frequency COMB light combined by the optical splitter is detected by an image sensor which functions as the optical detector or an image sensor which is positioned separate from the optical detector,
the focal point of the frequency COMB light which is output toward the measured object is regulated by a variable focal point lens which is positioned between the optical splitter and the measured object.

8. An apparatus for shape measurement of claim 4, wherein the apparatus is an optical coherence tomography system.

9. A frequency COMB light generator comprising:
a laser light source;
an optical resonator for generating a frequency COMB light from the laser light which is output by the laser light source;
a COMB pitch regulator for varying the frequency pitch of a frequency COMBs which constitutes the frequency COMB light; and
an output port for outputting a resonant output from the optical resonator; and
wherein the laser light which is output from the laser light source is modulated so that the frequency has a predetermined width,
the optical resonator includes:
an optical modulator for modulating the light by a modulation electrode;
a first mirror which is positioned at one end of a light waveguide of the optical modulator;

an optical fiber which is drawn out form the other end of the light waveguide of the optical modulator;

a second mirror which is positioned at the end of optical fiber, the COMB pitch regulator is a modulation signal generator for varying the modulation signal which is fed to the modulation electrode, and the second mirror is an apparatus for compensating the change in the polarization condition, or the optical fiber is a polarization maintaining fiber.

10. A frequency COMB light generator of claim 9 wherein further comprising:

a circulator having a first port, a second port and a third port which is positioned between the laser light source and the optical resonator, the laser light source is connected to the first port through an optical fiber, the optical resonator is connected to the second port through a polarization maintaining fiber, and the third port is the output port for the frequency COMB light, the first mirror is positioned on the light waveguide of the optical modulator at the side of the circulator, the second mirror is a Faraday rotation mirror, and positioned at the end of a predetermined length of the optical fiber which has no polarization maintaining function, the optical fiber is connected to the light waveguide of the optical modulator at the opposite side of the first mirror.

11. A frequency COMB light generator of claim 10, wherein the optical fiber is equipped with an optical fiber amplifier.

12. A frequency COMB light generator of claim 9, wherein further comprising:

an isolator having two ports which is positioned between a laser light source and an optical resonator, the laser light source is connected to one port through an optical fiber, the optical resonator is connected to the other port through a polarization maintaining fiber, wherein the first mirror is positioned on the light waveguide of the optical modulator at the side of the other port of the isolator, the second mirror is an output port for the frequency COMB light, and positioned at the end of a predetermined length of a polarization maintaining fiber, the optical fiber is connected to the light waveguide of the optical modulator at the opposite side of the first mirror, a polarization maintaining fiber amplifier is mounted on the polarization maintaining fiber.

* * * * *